United States Patent [19]
Kozaki et al.

[11] Patent Number: 5,945,331
[45] Date of Patent: Aug. 31, 1999

[54] MICROORGANISMS, AND METHOD FOR BIODEGRADATION OF ORGANIC COMPOUNDS AND METHOD FOR ENVIRONMENTAL REMEDIATION

[75] Inventors: Shinya Kozaki, Sakurashin-machi; Tetsuya Yano, Atsugi; Takeshi Imamura, Chigasaki, all of Japan

[73] Assignee: Canon Kabushiki Kaisha, Tokyo, Japan

[21] Appl. No.: 08/902,941

[22] Filed: Jul. 30, 1997

[30] Foreign Application Priority Data

Aug. 1, 1996 [JP] Japan .................................. 8-203653

[51] Int. Cl.$^6$ .............................. C12S 13/00; C12R 1/15
[52] U.S. Cl. .................. 435/262; 435/262.5; 435/252.5; 435/843
[58] Field of Search ..................................... 435/170, 174, 435/182, 262, 262.5, 874, 843, 252.1, 252.5, 253.3

[56] References Cited

U.S. PATENT DOCUMENTS

| | | | |
|---|---|---|---|
| 4,877,736 | 10/1989 | Fliermans ................................ | 435/183 |
| 4,925,802 | 5/1990 | Nelson et al. ........................... | 435/262 |
| 5,079,166 | 1/1992 | Winter et al. ........................... | 435/262 |
| 5,658,795 | 8/1997 | Kato et al. ............................. | 435/262.5 |
| 5,665,597 | 9/1997 | Imamura et al. ..................... | 435/258.3 |
| 5,679,568 | 10/1997 | Imamura et al. ..................... | 435/262.5 |
| 5,686,291 | 11/1997 | Ohkawa et al. ....................... | 435/262.5 |

FOREIGN PATENT DOCUMENTS

| | | |
|---|---|---|
| 0694611 | 1/1996 | European Pat. Off. . |
| 0 730 027 | 9/1996 | European Pat. Off. . |
| 2-92274 | 4/1990 | Japan . |
| 2-503866 | 11/1990 | Japan . |
| 3-292970 | 12/1991 | Japan . |
| 4-502277 | 4/1992 | Japan . |
| 6-22769 | 2/1994 | Japan . |
| 6-70753 | 3/1994 | Japan . |
| 6-105691 | 4/1994 | Japan . |
| 7-123976 | 5/1995 | Japan . |
| 7-236895 | 9/1995 | Japan . |
| 8-66182 | 3/1996 | Japan . |
| 8-294387 | 11/1996 | Japan . |
| WO90-06901 | 6/1990 | WIPO . |
| WO92-19738 | 11/1992 | WIPO . |

OTHER PUBLICATIONS

Munakata–Marr, et al. "Enhancement of Trichloroethylene Degradation . . . PR1", Envir. Sci. Technol., 1996, 30, 2045–2052.
Uchiyama, et al. "Aerobic Degradation of Trichloroethylene . . . Strain M", Agric. Biol. Chem. 53 (11), 2903–2907, 1989.
Negoro, et al. Growth of Microalgae . . . and $NO_x$, Appl. Biochem. & Biotech., 28/29, 877–886 (1991).
Tsien, et al. "Biodegradation of Trichloroethelene by . . . OB3b", Appl. Environ. Microbiol., 55, (12), 3155–3161 (1989).
Henry, et al.; "Influence of Endogenous and Exogenous . . . Aquifier", Appl. & Environ. Microbiol., 57, (1), 236–244 (1991).
Harker, et al.; "Trichloroethylene Degradation . . . JMP134", Appl. & Environ. Microbiol., 56, (4), 1179–1181 (1990).
Wackett, et al., "Survey of Microbiol. Oxygenases: . . . Bacteria", Appl. & Environ. Microbiol., 55, (11), 2960–2964 (1989).
Nelson, et al., "Aerobic Metabolism of Trichloroethylene . . . Isolate", Appl. & Environ. Microbiol., 52, (2), 383–384 (1986).
Nelson, et al., "Biodegradation of Trichloroethylene . . . Pathway", Appl. & Environ. Microbiol., 53, (5), 949–954 (1987).
Little, et al., "Trichloroethylene Biodegradation . . . Bacterium", Appl. & Environ. Microbiol., 54, (4), 951–956 (1988).
Kamath, et al., "New Pathway for the Biodegradation . . . niger", Appl. & Environ. Microbiol., 56, (1), 275–280 (1990).
Sandt, et al., "Mobilization of the genetically . . . Drinking Water", Appl. & Environ. Microbiol., 57, (1), 194–200 (1991).
Wackett, et al., "Degradation of Trichloroethylene . . . F1", Appl. & Environ. Microbiol., 54, (7), 1703–1708 (1988).
Vandenbergh, et al., "Metabolism of Volatile Chlorinated . . . fluorescens", Appl. & Environ. Microbiol, 54, (10), 2578–2579 (1988).
Vannelli, et al., "Degradation of Halogenated . . . *Nitrosomonas europaea*", Appl. & Environ. Microbiol, 56, (4), 1169–1171 (1990).
Shields, et al., "Selection of a *Pseudomonas cepacia* . . . Trichloroethelene", Appl. & Environ. Microbiol., 58, (12), 3977–3982 (1992).
Ewers, et al., "Selection of trichloroethene (TCE) . . . by TCE", Arch. Microbiol., 154, (4), 410–413 (1990).
Nakajima, et al., "Novel Metabolite of Trichloroethylene . . . Pathway", Biosci. Biotech. Biochem., 56, (3), 486–489 (1992).Nakajima, et al., "Purification and Properties . . . Methylocystis", Biosci. Biotech. Biochem., 56, (5), 736–740 (1992).
Int. J. Systm. Bact., 39, (3), 369–70 (1989).

(List continued on next page.)

*Primary Examiner*—William H. Beisner
*Attorney, Agent, or Firm*—Fitzpatrick, Cella, Harper & Scinto

[57] ABSTRACT

Novel microorganism strains JM2N (FERM BP-5961), JM6U (FERM BP-5962) and JM7 (FERM BP-5975), mutants of strain J1 (FERM BP-5102), constitutively expressing an oxygenase, and a method for biodegradation of organic compounds and a method for environmental remediation by decomposing pollutants in the environment using these novel microorganisms. These microorganisms do not require any inducer to express their organic compound-degrading ability, and use of these microorganisms enables effective decomposition of organic compounds and environment remediation.

66 Claims, 1 Drawing Sheet

OTHER PUBLICATIONS

Winter, et al., "Efficient Degradation of Trichloroethylene . . . *Coli*", Bio/Technology, 7, pp. 282–285 (1989).

Beam, et al., "Microbial Degradation of . . . Commensalism", J. Gen. Microbiol., 82, 163–169 (1974).

Hanson, et al., "Development of Methanotrophs . . . Chlorinated Olefins", Preprinted Extended Abstract, Div. Env. Chem., A.C.S. Miami Beach, Fla., pp. 365–367, Sep. 10–15, 1989.

Journal of Japan Sewage Works Assoc., 24, 273, 27–32 (1987).

Japance Patent Abstracts, Ab. No. JP409098775A of Okhawa et al. JP 09–098775 (Apr. 1997).

Krumme, et al., "Degradation . . . Microcosms", Appl. & Envir. Microb., 59, 8 (Aug. 1993).

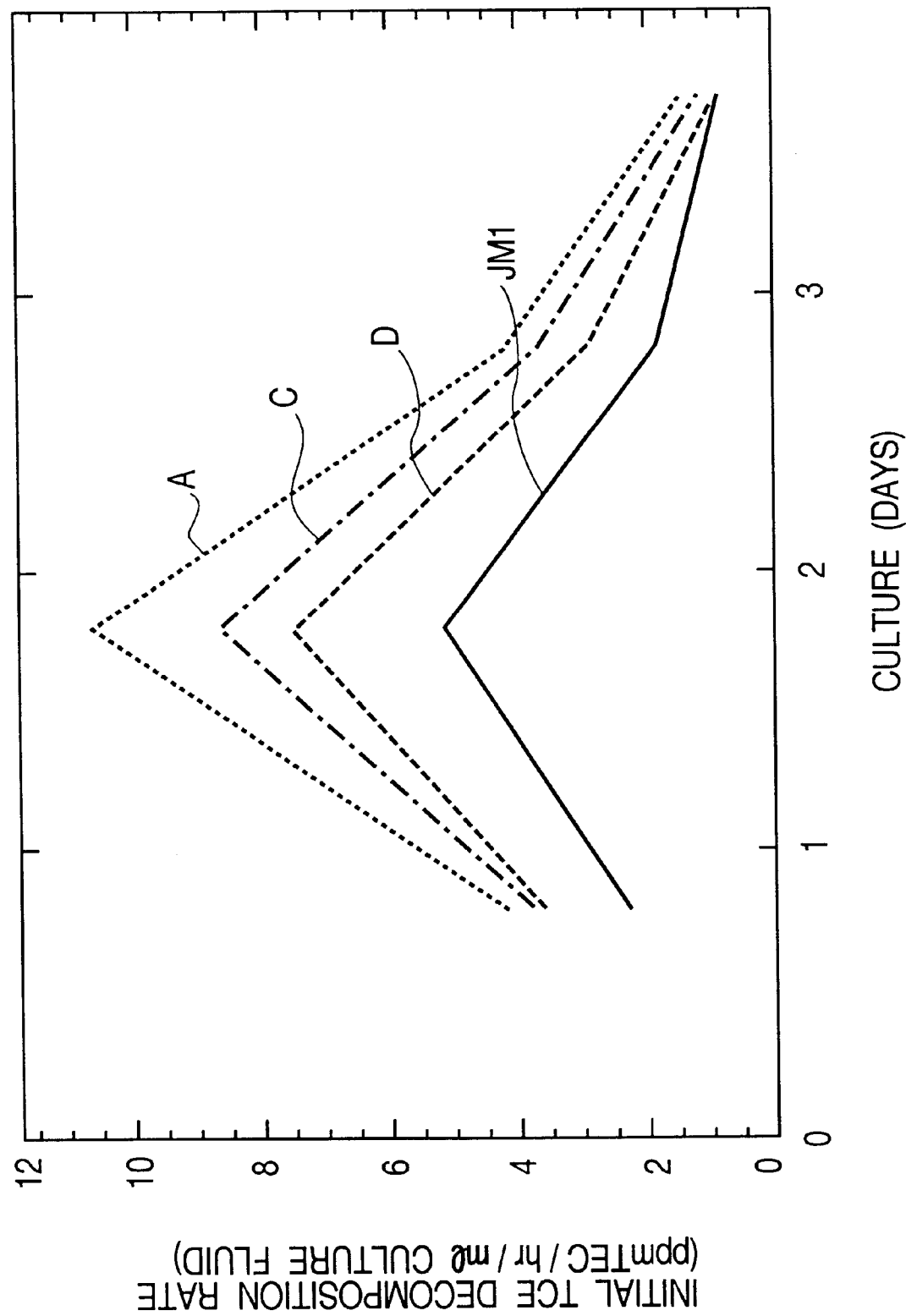

1

MICROORGANISMS, AND METHOD FOR BIODEGRADATION OF ORGANIC COMPOUNDS AND METHOD FOR ENVIRONMENTAL REMEDIATION

BACKGROUND OF THE INVENTION

1. Field of the Invention

This invention relates to a novel microorganism, and methods for biodegradation of organic compounds and for environmental remediation.

2. Related Background Art

Environmental pollution with hardly decomposable organic compounds that are toxic for organisms has become a serious problem in recent years. It is thought that pollution of soil with volatile chlorinated aliphatic hydrocarbon compounds such as tetrachloroethylene (PCE), trichloroethylene (TCE) and dichloroethylene (DCE) has been spreading considerably at the sites of paper and pulp industries, precession instrument industries and related industries in the world. Actually, it is often reported that these pollutants were detected through environmental surveys. It is supposed that these residual organic compounds in the soil are dissolved into rainwater and permeate into ground water, thereby spreading over surrounding area. Since these compounds are suspected to be carcinogenic besides being quite stable in the environment, contamination of ground water that is used as a source of drinking water especially has become a serious social problem. Therefore, cleaning of aqueous media such as contaminated ground water, and the soil and surrounding atmosphere by eliminating or decomposing polluting organic compounds is an important theme for environmental protection, and technologies required for cleaning the environment have been developed. For example, an absorption treatment with activated carbon and decomposition treatment by light or heat have been studied, but they are not always practical from the viewpoint of treatment cost and operability.

Recently, microbial decomposition of chlorinated organic compounds like TCE which are stable in the environment has been reported, and studies for its practical application have been started. The biodegradation method has several advantages that halogenated organic compounds can be decomposed into harmless substances by selecting appropriate microorganisms, specific chemicals are not needed and the maintenance cost and labor for the process can be saved.

Examples of microorganisms capable of decomposing TCE are Welchia alkenophila sero 5 (U.S. Pat. No. 4,877,736, ATCC 53570), Welchia alkenophila sero 33 (U.S. Pat. No. 4,877,736, ATCC 53571), Methylocystis sp. strain M (Agric Biol. Chem., 53, 2903 (1989), Biosci. Biotech. Biochem., 56, 486 (1992), ibid 56, 736 (1992)), Methylosinus trichosporium OB3b (Am. Chem. Soc. Natl. Meet. Dev. Environ. Microbiol., 29, 365 (1989), Appl. Environ. Microbiol., 55, 3155 (1989), Appl. Biochem. Biotechnol., 28, 877 (1991), Japanese Laid-Open Patent Application No. 2-92274, Japanese Laid-Open Patent Application No. 3-292970), Methylomonas sp. MM2 (Appl. Environ. Microbiol., 57, 236 (1991)), Alcaligenes denitrificans ssp. xylosoxidans JE75 (Arch. Microbiol., 154, 410 (1990)), Alcaligenes eutrophus JMP134 (Appl. Environ. Microbiol., 56, 1179 (1990)), Alcaligenes eutrophus FERM-13761 (Japanese Laid-Open Patent Application No. 7-123976), Pseudomonas aeruginosa JI104 (Japanese Laid-Open Patent Application No. 7-236895), Mycobacterium vaccae JOB5 (J. Gen. Microbiol., 82, 163 (1974), Appl. Environ. Microbiol., 55, 2960, (1989), ATCC 29678), Pseudomonas putida BH (J. of Japan Sewage Work Assoc. (Gesuido Kyokai-shi), 24, 27 (1987), Pseudomonas sp. strain G4 (Appl. Environ. Microbiol., 52, 383, (1986), ibid 53, 949 (1987), ibid 54, 951 (1989), ibid 56, 279 (1990), ibid 57, 193 (1991), U.S. Pat. No. 4,925,802, ATCC 53617, this strain was first classified as Pseudomonas cepacia but later changed to Pseudomonas sp.), Pseudomonas mendocina KR-1 (Bio/Technol., 7, 282 (1989), Pseudomonas putida F1 (Appl. Environ. Microbiol., 54, 1703 (1988), ibid 54, 2578 (1988)), Pseudomonas fluorescens PFL12 (Appl. Environ. Microbiol., 54, 2578 (1988)), Pseudomonas putida KWI-9 (Japanese Laid-Open Patent Application No. 6-70753), Pseudomonas cepacia KK01 (Japanese Laid-Open Patent Application No. 6-22769), Nitrosomonas europaea (Appl. Environ. Microbiol., 56, 1169 (1990)) and Lactobacillus vaqinalis sp. nov (Int. J. Syst. Bacteriol., 39, 368 (1989), ATCC 49540).

The problem in practically applying these decomposing bacteria for remedying the environment is that they require chemicals such as aromatic compounds or methane as an induction substance (an inducer).

Although aromatic compounds such as phenol or toluene are very excellent inducers, an intensive control is necessary when these compounds are discharged into the environment because they have toxicity. Methane is a flammable gas so that there is danger and difficulty in introducing it into the environment with control.

To solve the problems described above, Nelson et. al. developed a method to use tryptophan, an amino acid as an inducer for decomposition of volatile chlorinated organic compounds (Japanese Laid-Open Patent Application No. 4-502277). Although this method can avoid the toxicity and danger of the inducer itself to some extent, tryptophan is a very expensive compound, and the difficulty of introducing a specific substance into the environment with control is not still solved. Adding excess carbon and nitrogen source into the environment is also not preferable from the view point of eutrophication. Furthermore, since such TCE decomposition enzymes are inducible enzymes, the enzymatic activity once induced is usually sustained for from only several hours to a day, requiring another induction after that, and there is a problem that decomposition of TCE is competitively inhibited by the presence of the inducing agents.

Recently, there has been attempted to introduce an plasmid having a DNA fragment encoding oxygenase or hydroxylase as a TCE decomposition enzyme into a host bacterium in order to express the TCE decomposition activity using a harmless inducer or to constitutively express it in the absence of any inducers. For example, such DNA fragments are derived from Pseudomonas mendocina KR-1 (Japanese Laid-Open Patent Application No. 2-503866), Pseudomonas putida KWI-9 (Japanese Laid-Open Patent Application No. 6-105691) and Pseudomonas putida BH (Summary of 3rd Conference on Pollution of Ground Water/Soil and Its Protective Countermeasure, p.213 (1994).

These recombinant strains, however, have such problems that a very expensive IPTG (isopropyl thiogalactopyranoside) is required as an inducer or stability of the plasmid in the host bacterium strain is not sufficient. Moreover, the discharge of recombinant strains into the environment is under certain regulations considering the public acceptance.

To solve these problems, Seals et. al. obtained a mutant strain of Pseudomonas sp. G4 having a TCE decomposition activity without requiring any inducer (phenol or toluene in this case) by a method using a transposon (Appl. Environment. Microbiol., 58, 3977 (1992), PCT Application, International Publication No. WO 92/19738). The TCE decomposition activity of this G4 mutant is, however, is not sufficient apart from the problem of instability due to the transposon. Since the transposon itself contains an antibiotic resistance gene such as kanamycin resistance, there may be some undesirable effects by a horizontal transmission to other microorganisms when the mutant strain is released into the environment.

As a countermeasure of this problem, it is reported in Environmental Science & Technology, Vol. 30, No. 6, 1986, pp. 2045–2052 that a mutant, Burkholderia (Pseudomonas) cepacia $PR1_{301}$ (denoted as "$PR1_{301}$" hereinafter), which can decompose TCE without inducers, was obtained by mutagenizing the above strain G4 using nitrosoguanidine instead of genetic manipulation. However, according to the data of the above report, for example, FIG. 3 in the right column in page 2048 or FIG. 7 in the left column in page 2050, the TCE degradation ability of $PR1_{301}$ is in ppb order, insufficient for the remediation of the environment polluted with TCE.

As hitherto described, the bacterial species known in the art are not always satisfactory from the viewpoint that a microorganism not requiring inducers should satisfy practical conditions required for the decomposition of aromatic compounds or volatile chlorinated organic compounds and should express a sufficient decomposition ability. Therefore, there is an urgent need of obtaining microorganisms having practically required characteristics. Preferably, these microorganisms have such properties that they have a sufficient ability to degrade a pollutant such as aromatic compounds and halogenated aliphatic hydrocarbon compounds, and their growth conditions are different from the conventional microorganisms known in the art so that their application range or application form can be more expanded. During the treatment of liquid wastes or soil containing TCE using a microorganism, it is required for the microorganism to proliferate under poor conditions such as liquid waste or soil, while maintaining the required TCE-degrading activity.

SUMMARY OF THE INVENTION

As mentioned above, microbial species having a sufficient decomposition ability of aromatic compounds and/or chlorinated aliphatic hydrocarbon compounds, and having practically advantageous characteristics over the conventional microbial species are urgently required.

Accordingly, the object of the present invention is to provide a novel microorganism capable of decomposing aromatic compounds or chlorinated aliphatic hydrocarbon compounds without using any inducers.

The other object of the present invention is to provide a method for effective biodegradation of organic compounds.

The further object of the present invention is to provide a method for effective remediation of the environment by biodegradation of pollutants in the environment.

According to a first aspect of the present invention, there is provided a novel microorganism JM2N (FERM BP-5961) constitutively expressing an oxygenase, a mutant of strain J1 (FERM BP-5102).

According to a second aspect of the present invention, there is provided a method for biodegradation of aromatic compounds or chlorinated aliphatic hydrocarbon compounds by employing a novel microorganism JM2N (FERM BP-5961) constitutively expressing an oxygenase, a mutant of strain J1 (FERM BP-5102).

According to these aspects, organic compounds are quite effectively biodegraded even in the presence of other microorganisms.

According to a further aspect of the present invention, there is provided a method for remedying an environment contaminated with a pollutant comprising: decomposing the pollutant by employing a novel microorganism JM2N (FERM BP-5961) constitutively expressing an oxygenase, a mutant of strain J1 (FERM BP-5102).

According to this aspect, pollutants can be effectively biodegraded even in the environment where other microorganisms are coexisting, thereby remedying polluted environment in high efficiency.

According to a further aspect of the present invention, there is provided a novel microorganism JM6U (FERM BP-5962) constitutively expressing an oxygenase, a mutant of strain J1 (FERM BP-5102).

According to a further aspect of the present invention, there is provided a method for biodegradation of aromatic compounds or chlorinated aliphatic hydrocarbon compounds by employing a novel microorganism JM6U (FERM BP-5962) constitutively expressing an oxygenase, a mutant of strain J1 (FERM BP-5102).

According to these aspects, organic compounds are relatively effectively biodegraded even in the presence of other microorganisms.

According to a further aspect of the present invention, there is provided a method for remedying an environment contaminated with a pollutant comprising: decomposing the pollutant by employing a novel microorganism JM6U (FERM BP-5962) constitutively expressing an oxygenase, a mutant of strain J1 (FERM BP-5102).

According to this aspect, the pollutants are relatively effectively degraded even in the environment coexisting other microorganisms, thus remediating the polluted environment in relatively high efficiency.

According to a further aspect of the present invention, there is provided a novel microorganism JM7 (FERM BP-5957) constitutively expressing an oxygenase, a mutant of strain J1 (FERM BP-5102).

According to a further aspect of the present invention, there is provided a method remedying an environment polluted with a pollutant comprising: decomposing the pollutant by employing a novel microorganism JM7 (FERM BP-5957) constitutively expressing an oxygenase, a mutant of strain J1 (FERM BP-5102).

According to these aspects, organic compounds are effectively biodegraded even in the presence of other microorganisms.

According to a further aspect of the present invention, there is provided a method for remedying an environment polluted with a pollutant by employing a novel microorganism JM7 (FERM BP-5957) constitutively expressing an oxygenase, a mutant strain J1 (FERM BP-5102).

According to this aspect, organic compounds are effectively degraded even in the presence of other microorganisms.

BRIEF DESCRIPTION OF THE DRAWINGS

FIGURE is a graph representing the rate of TCE degradation in each growth phase of the strain JM2N, strain JM6U, strain JM7, and strain JM1.

DETAILED DESCRIPTION OF THE PREFERRED EMBODIMENTS

The various embodiments of the invention will now be further described hereinafter.

The inventors of this invention disclosed strain J1 (FERM BP-5102) in Japanese Laid-Open Patent Application No. 8-66182 as a microorganism capable of effectively decomposing aromatic compounds such as phenol or chlorinated aliphatic hydrocarbon compounds such as trichloroethylene in the presence of an inducer such as phenol. By mutagenizing strain J1 with a mutagen, the inventors of this invention obtained a novel strain JM1 (FERM BP-5352), a mutant of strain J1, that is able to decompose aromatic compounds or chlorinated aliphatic hydrocarbon compounds without any inducer, although the microbiological characteristics are identical to strain J1. From further investigations on the mutant strains induced by mutagenization of strain J1, the investigators of this invention obtained three more strains which constitutively express an oxygenase and identical with strain JM1 in microbiological characteristics but different from strain JM1 in, for example, in the decomposition ability for organic compounds in the unsterilized soil and in the growth rate in a culture medium of the same carbon source. These three strains are different from each other in their degradation abilities of organic compounds and in the growth rate in a culture medium of the same source, maintaining these properties after the prolonged subculture of each strain. Therefore, these three strains were recognized to be novel strains different from the strain JM1 and were given the names of strain JM2N, strain JM6U and strain JM7, and deposited in National Institute of Bioscience and Human Technology, Agency of Industrial Science and Technology (FERM BP-5961, FERM BP-5962 and FERM BP-5957), respectively.

The address of the depository is 1–3, Higashi 1-chome, Tsukuba-shi, Ibaraki-ken, 305 Japan. Strain JM2N (FERM BP-5961) was deposited in Jun. 13, 1996; Strain JM6U (FERM BP-5962) was deposited on Jun. 13, 1996 and Strain JM7 (FERM BP5957) was deposited on Jun. 13, 1997.

The microbiological characteristics of these novel three strains are listed below.
Microbiological characteristics
Gram's staining and morphology: Gram-negative, rods
Growth on culture medium:
    BHIA: good
    MacConkey: possible
Color of colony: Creamy color
Optimum temperature: 25° C.>30° C.>35° C.
Motility: negative (in semi-solid medium)
TSI (slant/butt): alkali/alkali, H2S(−)
Oxidase: positive (weak)
Catalase: positive
Fermentation of sugars:
    glucose: negative
    sucrose: negative
    raffinose: negative
    galactose: negative
    maltose: negative
Urease: positive
Esculin hydrolysis (β-glucosidase): positive
Silver nitrate reduction: negative
Indole production: negative
Glucose oxidation: negative
Arginine dihydrolase: negative
Gelatin hydrolysis (proteinase): negative
β-galactosidase: negative
Assimilation of each compound
    glucose: negative
    L-arabinose: negative
    D-mannose: negative
    D-mannitol: negative
    N-acetyl-D-glucosamine: negative
    maltose: negative
    potassium glucuronate: negative
    n-capric acid: positive
    adipic acid: negative
    dl-malic acid: positive
    sodium citrate: positive
    phenyl acetate: negative It should be noted that the previously mentioned $PR1_{301}$ and the strains of the present invention, JM2N (FERM BP-5961), JM6U (FERM BP-5962) and JM7 (FERM BP-5957), are completely different strains. Although any microbiological characteristics of $PR1_{301}$ are not described in Environmental Science & Technology, VOL. 30, No. 6, 1986, pp 2045–2052 that describes $PR1_{301}$, it is described that $PR1_{301}$ is a spontaneous revertant of Burkholderia cepacia $G4_{301}$ which was obtained by mutagenizing Burkholderia cepacia G4 with N-methyl-N'-nitrosoguanidine (NTG). Therefore, the microbiological characteristics of $PR1_{301}$ are considered to be identical with the parent strain, strain G4. The microbiological characteristics of the strain G4 are as follows according to the description in WO90/06901.
Gram staining and morphology: Gram-negative, rods
urease: negative
esculin hydrolysis (β-glucosidase): negative
silver nitrate reduction: positive
indole production: negative
Glucose oxidation: negative
Arginine dihydrolase: negative
Gelatin hydrolysis: negative
β-Galactosidase: negative
Assimilation of compound
    L-arabinose: positive
    D-mannose: positive
    D-mannitol: positive
    N-acetyl-D-glucosamine: positive
    maltose: negative
    potassium glucuronate: positive
    n-capric acid: positive
    adipic acid: negative
    dl-malic acid: positive
    sodium citrate: ±
    phenyl acetate: positive Since the microbiological characteristics of the strain G4 described above are clearly different from those of the strains JM2N, JM6U and JM7 of this invention, it is concluded that $PR1_{301}$ is a completely different strain from the strains JM2N, JM6U and JM7.

Each of the strain JM2N, JM6U and JM7 degrades chlorinated aliphatic hydrocarbon compounds as well as aromatic compounds such as phenol and cresol, indicating that these strains naturally have a resistivity against these compounds. As is evident from the fact that these compounds are usually used as a sterilizer, these compounds are harmful to most microorganisms. Although these compounds are often contained in waste liquid, the strains JM2N, JM6U and JM7 would not die out nor the activity be inhibited even in the presence of these chemicals, enabling decomposition of volatile chlorinated organic compounds.

In decomposing volatile chlorinated organic compounds in the environment like groundwater and soil, no inducer such as phenol is needed but conventional nutrients, thereby making the operation simple besides solving the problem that toxic and highly dangerous inducers are released in the environment. In addition, oxygenase, an enzyme which degrades volatile chlorinated organic compounds, does not suffer a competitive inhibition with aromatic compounds, thereby effectively degrading volatile chlorinated organic compounds only.

The nutrients used for cultivating JM2N, JM6U and JM7 according to this invention may be any carbon source, nitrogen source and inorganic salts, provided they are required for ordinary microbial culture and assimilable by the microorganisms of the present invention. For example, M9 medium supplemented with yeast extract for some nutrients can be used. The composition of M9 medium is as follows:

$Na_2HPO_4$: 6.2 g
$KH_2PO_4$: 3.0 g
NaCl: 0.5 g
$NH_4Cl$: 1.0 g
in 1 liter of culture medium; pH 7.0.

Cultivation may be carried out under anaerobic conditions by either a liquid cultivation or solid cultivation. The preferable culture temperature is around 30° C.

Method for Obtaining Microorganisms

The method used to obtain novel microbial strains JM2N, JM6U and JM7 of the present invention is explained. Such strains can be obtained by subjecting strain J1 (FERM BP-5102) to a mutagenization process using a mutagen.

Any mutagen known in the art can be used as physical or chemical mutagens, for example, ultraviolet light as a physical mutagen, N-methyl-N'-nitro-N-nitrosoguanidine, ethyl methanesulfonate, nitrite or acridine dye as a chemical mutagen.

Methods for Decomposing Organic Compounds and Environmental Remediation

The decomposition treatment of organic compounds (for example, aromatic compounds and chlorinated aliphatic hydrocarbon compounds) using the novel microbial strains of this invention can be carried out by allowing the organic compounds in an aqueous medium, soil and air to contact the microorganisms described above. Any method for contacting the microorganisms with the organic compounds can be used, provided the microorganisms can exhibit their decomposition activities, a batch method, semi-continuous method or continuous method being applicable. The microorganisms may be used in semi-immobilized state or may be immobilized on an appropriate carrier. The objects to be treated such as waste liquid, soil or air can be subjected to some pre-treatment, if necessary.

Decomposition of Organic Compounds or Pollutants in an Aqueous Medium

The decomposition treatment of the aromatic organic compounds or chlorinated aliphatic hydrocarbon compounds in an aqueous medium according to this invention can be carried out by allowing the aromatic compounds and/or volatile chlorinated organic compounds present in the aqueous medium to contact with the strains JM2N, JM6U and JM7 described above. While representative embodiments for application are described hereinafter, the microorganisms of this invention can be used for any purification treatment of the aromatic compounds and/or volatile chlorinated organic compounds in the aqueous medium, not limited to these embodiments.

The most simple method is, for example, to directly introduce the strain JM2N, JM6U or JM7 into the aqueous medium polluted with aromatic compounds and/or volatile halogenated organic compounds. Although it is preferable to adjust pH, salt concentration, temperature and concentration of pollutants in the aqueous medium, the strains JM2N, JM6U and JM7 can maintain their decomposition activity unless the environment is under extremely acidic or alkaline conditions or high salt concentration. They can proliferate also at around 15° C. that is thought to be an average temperature of ground water in Japan, while maintaining their decomposition activity.

In another application embodiment, a fermentation vessel is provided to culture strain JM2N, JM6U or JM7, wherein an aqueous medium polluted with aromatic compounds and/or volatile chlorinated organic compounds are introduced for decomposition at a prescribed flow rate. Introduction and discharge of the aqueous medium may be carried out continuously, intermittently or batchwise, depending on the treatment capacity, and such a system control can optimize the decomposition system in compliance with the concentration of aromatic compounds and/or volatile halogenated organic compounds.

In other embodiment, strains JM2N, JM6U and JM7 are attached to a carrier, for example soil particles, followed by filling the carrier in a reaction vessel, into which an aqueous medium polluted with organic compounds is introduced for decomposition treatment. For this purpose, any carrier can be used as a carrier as well as the soil particles, but those having a high holding capacity for microorganisms and being not obstructive for aeration are more preferable. For example, various microbial carriers commonly used for bioreactors in medical industries, food industries and waste liquid processing can be also used as materials which provide inhabitable spaces for a microorganism.

Specifically, such carriers include inorganic granular carriers such as porous glass, ceramics, metal oxides, activated carbon, kaolinite, bentonite, zeolite, silica gel, alumina and anthracoid; gel state carriers such as starch, agar, chitin, chitosan, polyvinyl alcohol, alginic acid, polyacrylamide, carrageenan, agarose and gelatin; ion-exchange cellulose, ion-exchange resin, cellulose derivatives, glutaraldehyde, polyacrylic acid, polyurethane and polyester. Natural cellulose materials such as cotton, hemp or paper, or natural lignin materials such as saw dust or barks are also available for use.

Decomposition of Organic Compounds and Pollutants in Soil

According to the present invention, decomposition treatment of aromatic compounds and/or volatile chlorinated organic compounds in soil is carried out by the contact of the aromatic compounds and/or volatile chlorinated organic compounds present in soil with strain JM2N (JM6U or JM7). Representative application embodiments are described hereinafter, these strains can be used for purifying aromatic compounds and/or volatile chlorinated organic compounds in any soil without being limited by these embodiments.

A comparatively simple and preferable method comprises directly introducing strain JM2N, JM6U or JM7 into the soil polluted with aromatic compounds and/or volatile chlorinated organic compounds. As an introduction method, the microorganism is applied on the surface of soil, or introduced through a well dug deep into the earth when the treatment is carried out in a relatively deep stratum. When a pressure is applied by air or water, the microorganism can be more effectively spread in a wider zone. In this case, it is preferable to adjust the soil conditions suitable for strain JM2N, JM6U or JM7 to survive. It is also preferable to use a carrier for the microorganism, since the growth rate of strains JM2N, JM6U and JM7 increases in the presence of a carrier such as highly water-absorbent polymers etc.

Since these microorganisms proliferate at a temperature of 15° C. that is a mean temperature of the soil in Japan, they can maintain enough activity for decomposition of organic compounds and pollutants.

In another embodiment, strain JM2N, JM6U or JM7 is attached to a carrier, filled into a reaction vessel, and then introduced into the soil, mainly in the aquifer, contaminated with pollutants such as aromatic compounds and/or chlorinated aliphatic hydrocarbon compounds. The reaction vessel preferably takes a configuration such as a fence or a sheet of film so that it can cover a wide range in the soil. Carriers in this case can be made of hitherto described materials.

Degradation of Organic Compounds/Pollutants in the Vapor Phase

Pollutants in the vapor phase can be degraded by contacting the pollutants present in the vapor phase with strain JM2N, JM6U or JM7. While representative embodiments for degradation are described below, this invention is not limited to them but the strains according to this invention are applicable for any purification treatment of aromatic compounds and/or volatile chlorinated organic compounds in the vapor phase.

In one embodiment, strains JM2N, JM6U or JM7 are cultured in a culture vessel into which air polluted with pollutants is introduced at a prescribed flow rate to decompose the pollutants. While the method for introduction is not limited, it is more preferable that the culture medium is agitated by introducing air to facilitate aeration. Air may be introduced or exhausted continuously, but treatments by a batch method or interval method is also possible depending on the treatment capacity of the vessel, and such a system control can optimize the decomposition system in compliance with the concentration of aromatic compounds and/or volatile halogenated organic compounds.

In another embodiment, strain JM2N, JM6U or JM7 is attached to a carrier, soil particles, for example, filled into a reaction vessel, to which the air contaminated with aromatic compounds and/or volatile chlorinated compounds is introduced to decompose the pollutants. Carriers as mentioned above can be used for this purpose.

In addition, as the carrier materials which can both hold and feed the microorganism, there are compost that is frequently used in agriculture, forestry and fishery; plant dry stuffs such as crop straws, saw dust, rice bran, soy bean curd waste and bagasse; and marine wastes such as crab shells or lobster shells.

For purifying polluted air, the microorganism may be introduced into a vessel filled with a carrier or after a preliminary culture with the carrier. Reaction conditions such as nutrients, water content and oxygen concentration should be desirably maintained for the effective decomposition reactions. The ratio between the volume of the carrier and water content in the reaction vessel may be selected considering the microbial growth and aeration efficiency, and the shape of the reaction vessel can be appropriately determined depending on the volume and pollutant concentration of the air to be treated. Anyway, these conditions are determined to facilitate contacting air with the microorganism retained on the carrier. Reaction vessels in the shape of a column, tube, tank or box are advantageously used. The reaction vessel of such a configuration may be constructed into a unit together with a ventilation duct or an air filter, optionally being connected in series depending on their capacity.

Polluted air may be adsorbed by the carrier material at first, and the effect of the microorganism cannot be observed in rare cases. However, it is said that the pollutant adsorbed on the carrier is decomposed after a certain period of time, and new pollutant is adsorbed on the surface of the carrier from which the first pollutant was removed by decomposition, thereby regenerating the absorption capacity of the carrier. Thus, a constant decomposition rate is expected without saturation of the pollutant-eliminating ability.

Conventional microbial culture media can be used for the proliferation of the microorganism of this invention for purification of pollutants. For example, bouillon medium, M9 medium, 2×YT medium, L medium or a medium containing polypeptone, yeast extract and carbon sources such as sugars and organic acids in a proper ratio is effective. These media are effective in a liquid form or a gel form prepared by adding agarose to the liquid form.

The method according to this invention is applicable for the treatment of waste liquid, soil and air in a closed system or open system. Various methods for immobilizing the microorganism on the carrier or for facilitating the growth of the microorganism may be used together.

EXAMPLE 1

Preparation of Microbial Strains JM2N, JM6U and JM7

(1) Preparation of Microorganisms A, B and C by Mutagenization of Strain J1

Colonies of strain J1 on an agar medium were inoculated into 100 ml of M9 medium containing 0.1% of yeast extract and 200 ppm of phenol and cultured with shaking in a Sakaguchi flask at 30° C. for 18 hours. The 10 ml culture was centrifuged and the supernatant was removed. Then, 5 ml of M9 medium containing 20 ppm of NTG (N-methyl-N'-nitro-N-nitrosoguanidine) and 200 ppm of phenol was added to the cells and the cells were cultured with shaking at 30° C.

The culture started to yellow within 2 to 3 hours due to the formation of 2-hydroxymuconic acid semialdehyde, an intermediate degradation product of phenol. At this moment, the culture was spread on an M9 agar medium containing 100 ppm of indole and 0.1% of yeast extract, and incubated at 30° C.

Two days after, there were 25 colonies of deep-blue color due to indigo formed as an oxidation product of indole.

Each colony was isolated and inoculated in M9 medium only supplemented with 0.1% of yeast extract, and cultured with shaking at 25° C. for 24 hours. 10 ml of each culture was transferred into a 27.5 ml glass bottle. After sealing the bottle with a butyl rubber stopper and an aluminum cap, gaseous TCE was added in the bottle using a syringe, followed by shaking at 25° C. for TCE biodegradation. The initial concentration of TCE was 12 ppm assuming that all the TCE added had completely dissolved into the culture. TCE concentration of each culture medium after 6 hours was measured by gas chromatography (GC-14B made by Shimadzu Seisakusho Co., column: made by J&B Co.; DB-624).

Three reference samples, 1: M9 medium containing 0.1% of yeast extract but without cells, 2: a culture medium in which strain J1 was grown as described above, and 3: a culture medium in which strain JM1 was grown as described above, were prepared and a decomposition test of TCE using each reference sample was also carried out. As a result, there were three samples that exhibit identical TCE degradation abilities with that of the reference sample 3, and each sample is denoted as A, B and C hereinafter. The concentration of residual TCE in each three samples is shown in Table 1.

11

TABLE 1

| | Control 1 | Control 2 | Control 3 | Sample A | Sample B | Sample C |
|---|---|---|---|---|---|---|
| Concentration of residual TCE (ppm) | 11.7 | 11.2 | 1.1 | 1.1 | 1.4 | 1.2 |

(2) Comparison of Growth Rate of Microorganisms A, B and C, and Strain JM1

Each microorganism of the samples A, B and C (denoted as microorganisms A, B and C hereinafter) and strain JM1 were thoroughly adapted to M9 medium containing sodium malate. Specifically, each culture of sample A, B and C, and sample 3 was added into M9 medium containing 0.05% of yeast extract and 1% of sodium malate by 1/100 volume, and cultured for 48 hours at 25° C. Then the culture was added into M9 medium containing 2% of sodium malate by 1/100 volume and further cultured at 25° C. for 48 hours, which was repeated two more times. Then the culture obtained was added into M9 medium containing 2% of sodium malate by 1/100 volume and cultured for 72 hours at 15° C. The culture thus obtained was spread on an agar medium containing 1% of sodium malate and cultivated at 15° C. for 3 days. As a result, 10 to 15 colonies were formed on each agar medium. Each of microorganisms A, B and C showed a different colony size with each other, also different from the colony size of strain JM1. Mean colony sizes of microorganisms A, B and C, and strain JM1 are shown in Table 2.

TABLE 2

| | Strain JM1 | Microorganism A | Microorganism B | Microorganism C |
|---|---|---|---|---|
| Mean diameter of colony (mm) | 2.2 | 5.1 | 6.5 | 4.2 |

A colony of each sample grown on the agar medium was subcultured five times in M9 liquid medium containing 2% of sodium malate, and the final subculture was spread on M9 medium containing 1% of sodium malate and incubated at 15° C. for 3 days. The order of each mean colony size was strain B>strain A>strain C>strain JM1 as shown in Table 2, confirming that there is a clear difference between the growth rates of microorganisms A, B and C, as well as strain JM1, and the difference is maintained after the subculture of each sample.

(3) Comparison of degradation ability of microorganisms A, B and C, and strain JM1 on TCE in the soil Each colony of the microorganisms A, B and C, and strain JM1 grown on M9 medium containing 1% of sodium malate was inoculated in 200 ml of M9 medium containing 2% of sodium malate in a Sakaguchi flask, and cultured with shaking at 15° C. for 70 hours, thereby preparing each culture of microorganisms A, B and C, and strain JM1.

Each culture above was inoculated in M9 medium containing 2% of sodium malate by 1/100 volume to prepare cell suspensions of the microorganisms A, B and C, and strain JM1.

A plurality of 68 ml glass bottles were then prepared and 50 g of unsterilized Sawara sand (water content about 10%) was placed in each bottle. These glass bottles were divided into 4 groups and to bottles of each group one of the cultures of microorganisms A, B, C, and strain JM1 was added (5 ml each). After cultivating all the cotton-plugged glass bottles at 15° C. for 0.8 days, they were each sealed with a butyl rubber stopper and an aluminum cap.

Next, gaseous TCE was introduced into each bottle of each group with a syringe so that the concentration of TCE will be 50 ppm with the proviso that all TCE added is completely dissolved into water in the bottle. During incubating each glass added with TCE at 15° C., the time course of TCE concentration in the gaseous phase in each bottle was measured with gas chromatography for 3 hours from the TCE addition. TCE decomposition rate per 1 ml of water in the soil (assuming that the microorganism in the glass bottle distributes in water contained in the soil) and per unit time (ppm TCE/hour) was calculated from the results obtained.

The process described above was repeated except that the growth phase of during the decomposition of TCE was changed by changing the period of stationary cultivation from 0.8 days to 1.8 days, 2.8 days and 3.7 days. Each decomposition rate (ppm TCE/hour/ml) of microorganisms A, B and C, and strain JM1 corresponding to the stationary cultivation period of 1.8 days, 2.8 days and 3.7 days, respectively, expressed in per 1 ml of water contained in the soil (assuming that the microorganism in the glass bottle distributes in the water in the soil) and per unit time was calculated from the results obtained. As shown in Figure, the results indicated that, although the pattern according to the growth phase of each microorganism quite resembles with each other, TCE degradation rates were clearly different between the microorganisms A, B, C, and strain JM1.

Decomposition of TCE in the soil was also carried out by the same method as described above using the microorganisms A, B and C subcultured 5 times in M9 agar medium containing 1% of sodium malate. As a result, as shown in figure, the difference in TCE degradation rates of microorganisms A, B, C, and strain JM1 was still maintained.

From the facts that a significant difference in the growth rate on the same culture medium was observed between the microorganisms A, B and C, and strain JM1 as described in Example 1-(2), which difference was observed even after 5 subcultures, and that a significant difference in TCE decomposition rate was also observed between the microorganisms A, B and C, and strain JM1 as described in Example 1-(3), which difference was observed even after the subcultures, it was concluded that the microorganism A, B and C are different from strain JM1 and the microorganisms A, B and C are novel microorganisms different from each other. The microorganisms were therefore deposited in National Institute of Bioscience and Human Technology, Agency of Industrial Science and Technology (Tsukubashi, Ibaragi Prefecture) with the following discrimination and deposit numbers of the microorganisms A, B and C:

Microorganisms A: JM2N; FERM BP-5961
Microorganisms B: JM6U; FERM BP-5962
Microorganisms C: JM7; FERM BP-5957

Decomposition of Organic Compounds/Method for Environmental Remediation by Strain JM2N (Examples 2–4)

EXAMPLE 2

Decomposition of DCE in an Aqueous Solution using Strain JM2N

A colony of strain JM2N grown on M9 agar medium containing 1% of sodium malate was inoculated in 200 ml of M9 medium containing 2% of sodium malate in a Sakaguchi flask, and cultured with shaking at 15° C. for 70 hours.

A 10 ml aliquot of the above culture medium was added into a 27.5 ml glass bottle DCE decomposition was tested in the same manner as in Example 1-(1) except that cis-1,2-dichloroethylene (cis-1,2-DCE) and trans-1,2-dichloroethylene (trans-1,2-DCE) were added at 10 ppm, and 1,1-dichloroethylene (1,1-DCE) was added to 5 ppm instead of TCE. The concentration of residual DCEs after 6 hour cultivation was measured by the same method as used for the residual TCE described in Example 1-(1). The sample in which no microorganism was added was used as a reference sample. As listed in Table 3, the results showed that strain JM2N is able to advantageously decompose dichloroethylene.

TABLE 3

|  | Control (Without cells) | Strain JM2N |
| --- | --- | --- |
| cis-1,2-DCE | 98(%) | 11(%) |
| trans-1,2-DCE | 97 | 14 |
| 1,1-DCE | 91 | 18 |

EXAMPLE 3

Decomposition of Aromatic Compounds in an Aqueous Solution using Strain JM2N (Liquid Cultivation System)

Time course of concentration change of aromatic compounds was measured by the same method as in Example 2, except that the chemicals to be decomposed were 200 ppm of phenol, 200 ppm of o-cresol and 200 ppm of m-cresol (each added directly), and 50 ppm of toluene (added as a gas). The concentrations of phenol and cresol were measured by liquid chromatography while the concentration of toluene was measured by gas chromatography. The residual rate of each compound after 6 hours is shown in Table 4. The results in this example show that strain JM2N can degrade these aromatic compounds efficiently.

TABLE 4

|  | Control (Without Cells) | Strain JM2N |
| --- | --- | --- |
| Phenol | 99(%) | 9(%) |
| o-Cresol | 99 | 11 |
| m-Cresol | 98 | 11 |
| Toluene | 95 | 4 |

EXAMPLE 4

Degradation of TCE in the Vapor Phase by Aerating Culture Fluid of Strain JM2N

A colony of strain JM2N grown on M9 agar containing 1% of sodium malate as in Example 1-(2) was inoculated into a Sakaguchi flask containing 200 ml of M9 medium supplemented with 2% of sodium malate, and cultured with shaking at 15° C. for 70 hours.

A 30 ml aliquot of the above culture was placed in a 68 ml glass bottle, through which the air which had aerated a saturated solution of TCE was passed at a flow rate of 20 ml/min for 30 minutes. Then the bottle was completely sealed with a butyl rubber stopper and an aluminum cap and incubated with shaking at 30° C. The residual rate TCE after 24 hours was measured by gas chromatography.

As a control, the residual TCE in a similar system but containing no microbes was measured by gas chromatography. The results are shown in Table 5. It is evident from the result that strain JM2N can decompose TCE in the gas phase.

TABLE 5

|  | Control (Without Cells) | Strain JM2N |
| --- | --- | --- |
| Residual rate of TCE (%) | 94 | 42 |

Degradation of Organic Compounds by Strain JM6U/ Method for Environmental Remediation (Examples 5 to 7)

EXAMPLE 5

Degradation of DCE in an Aqueous Solution using Strain JM6U

The DCE degradation ability of strain JM6U was measured by the same method as in Example 2, except that strain JM2N in Example 2 was replaced with strain JM6U.

As a control, no microorganisms were added. The residual rate of DCE after the 6 hr incubation is shown in Table 6. The results in this example show that strain JM6U can degrade DCE.

TABLE 6

|  | Control (Without cells) | Strain JM6U |
| --- | --- | --- |
| cis-1,2-DCE | 96(%) | 25(%) |
| trans-1,2-DCE | 98 | 19 |
| 1,1-DCE | 94 | 22 |

EXAMPLE 6

Degradation of Aromatic Compounds in Aqueous Phase using Strain JM6U (Liquid Cultivation System)

Degradation of aromatic compounds was carried out in the same manner as in Example 3, except that the microorganism was changed from strain JM2N to strain JM6U. The residual rates of the aromatic compounds after 6 hr incubation are shown in Table 7. This Example shows that strain JM6U can degrade various aromatic compounds.

TABLE 7

|  | Control (Without cells) | Strain JM6U |
| --- | --- | --- |
| Phenol | 99(%) | 19(%) |
| o-Cresol | 99 | 22 |
| m-Cresol | 98 | 18 |
| Toluene | 96 | 12 |

EXAMPLE 7

Decomposition of TCE in the Air by Aerating the Liquid Culture of Strain JM6U

Decomposition of TCE in the air was carried out in the same manner as in Example 4, except that strain JM6U was used in place of JM2N. As a control, the residual rate of TCE in the similar experimental system containing no microbes was measured as in Example 4. The results are shown in Table 8. The results in this example show that TCE in the air can be decomposed by strain JM6U.

TABLE 8

|  | Control (Without cells) | Strain JM6U |
|---|---|---|
| Residual rate TCE(%) | 91 | 51 |

Decomposition of Organic Compounds using Strain JM7/ Method for Environmental Remediation (Examples 8 to 10)

EXAMPLE 8

Decomposition of DCE in an Aqueous Solution by Strain JM7

Decomposition of DCE was measured by the same method as in Example 2, except that strain JM7 was used instead of strain JM2N. As a control, an experimental system containing no microorganisms was used. The residual rate of DCE after 6 hr incubation is shown in Table 9. The results in this example show that strain JM7 can degrade DCE.

TABLE 9

|  | Control (No cells were added) | Strain JM7 |
|---|---|---|
| cis-1,2-DCE | 98(%) | 15(%) |
| trans-1,2-DCE | 97 | 18 |
| 1,1-DCE | 91 | 25 |

EXAMPLE 9

Decomposition of Aromatic Compounds in Aqueous Solution using JM7 (Liquid Cultivation System)

Decomposition of aromatic compounds was carried out in the same manner as in Example 3, except that strain JM7 was used instead of strain JM2N. The residual rates of aromatic compounds after 6 hr incubation are shown in Table 10. The results in this example show that strain JM7 can degrade various aromatic compounds.

TABLE 10

|  | Control (Without cells) | Strain JM7 |
|---|---|---|
| Phenol | 99(%) | 12(%) |
| o-Cresol | 99 | 14 |
| m-Cresol | 98 | 17 |
| Toluene | 95 | 7 |

EXAMPLE 10

Decomposition of TCE in the Air by Aerating the Liquid Culture of Strain JM7

Decomposition of TCE was carried out by the same method as in Example 4, except that strain JM7 was used instead of strain JM2N. As a control, the residual rate of TCE after 24 hours in the similar experimental system containing no microbes was measured. The results are shown in Table 11. The results in this example show that strain JM7 can degrade TCE in the air.

TABLE 11

|  | Control (Without cells) | Strain JM7 |
|---|---|---|
| Residual rate of TCE (%) | 94 | 51 |

As is evident from the descriptions above, the novel strains JM2N, JM6U and JM7 have abilities for decomposing organic compounds without any inducers.

By using these microorganisms, it is possible to effectively decompose organic compounds as well as enabling to effectively remedy the environment polluted with various pollutants such as organic compounds.

Furthermore, these microorganisms can effectively decompose pollutants in the unsterilized environment, thereby enhancing the efficiency of environmental remediation.

What is claimed is:

1. A biologically pure culture of microorganism strain JM2N identified by Deposit No. (FERM BP-5961), said strain JM2N being a mutant strain of strain J1 identified by Deposit No. (FERM BP-5102), and having an ability to degrade an aromatic compound and a chlorinated aliphatic hydrocarbon compound constitutively.

2. A method for biodegrading aromatic compounds or chlorinated aliphatic hydrocarbon compounds comprising: a step of bringing a biologically pure culture of microorganism strain JM2N identified by Deposit No. (FERM BP-5961) into contact with the compounds to be degraded, wherein the strain JM2N is a mutant strain of strain J1 identified by Deposit No. (FERM BP-5102), and capable of degrading an aromatic compound and a chlorinated aliphatic hydrocarbon compound constitutively.

3. A method according to claim 2, wherein said aromatic compounds are at least one organic compound selected from phenol, toluene and cresol.

4. A method according to claim 2, wherein said chlorinated aliphatic hydrocarbon compounds are at least one organic compound selected from trichloroethylene and dichloroethylene.

5. A method for remedying an environment contaminated with a pollutant comprising: a step of decomposing the pollutant by contacting with a biologically pure culture of microorganism strain JM2N identified by Deposit No. (FERM BP-5961), wherein the strain JM2 is a mutant strain of strain J1 identified by Deposit No. (FERM BP-5102), and capable of degrading an aromatic compound and a chlorinated aliphatic hydrocarbon compound constitutively.

6. A method according to claim 5 wherein said environment is an aqueous medium.

7. A method according to claim 6 wherein said aqueous medium is made to contact with a carrier on which said microorganism is retained.

8. A method according to claim 7 wherein the carrier retaining said microorganism is placed in a container, said aqueous medium being introduced from one side and discharged from the other side of the container.

9. A method according to claim 5, wherein said environment is a soil.

10. A method according to claim 9, wherein said microorganism is contained in an aqueous medium, said aqueous medium being introduced into the soil.

11. A method according to claim 10, wherein at least one of nutrients for said microorganism and oxygen is introduced into said soil.

12. A method according to claim 10, wherein said aqueous medium is introduced into the soil by applying a pressure through a injection well provided in the soil.

13. A method according to claim 10, wherein said microorganism is made to incorporate into a liquid phase, followed by introducing said soil into said liquid phase.

14. A method according to claim 10, wherein said soil is made to contact with a carrier retaining said microorganism.

15. A method according to claim 5, wherein said environment is air.

16. A method according to claim 15, wherein said air is introduced into a liquid phase incorporating said microorganism.

17. A method according to claim 15, wherein said air is made to contact with a carrier retaining said microorganism.

18. A method according to claim 15, wherein said air is introduced from one side and discharged from the other side of a container that contains a carrier retaining the microorganism.

19. A method according to claim 5, wherein said pollutant is aromatic compounds.

20. A method according to claim 19, wherein said aromatic compound is at least one of phenol, toluene or cresol.

21. A method according to claim 5, wherein said pollutant is chlorinated aliphatic hydrocarbon compounds.

22. A method according to claim 21, wherein said chlorinated aliphatic hydrocarbon compound is at least one of trichloroethylene or dichloroethylene.

23. A biologically pure culture of microorganism strain JM6U identified by Deposit No. (FERM BP-5962), said strain JM6U being a mutant strain of strain J1 identified by Deposit No. (FERM BP-5102), and having an ability to degrade an aromatic compound and a chlorinated aliphatic hydrocarbon compound constitutively.

24. A method for biodegrading aromatic compounds or chlorinated aliphatic hydrocarbon compounds comprising: a step of bringing a biologically pure culture of microorganism strain JM6U identified by Deposit No. (FERM BP-5962) into contact with the compounds to be degraded, wherein the strain JM6U is a mutant strain of strain J1 identified by Deposit No. (FERM BP-5102), and capable of degrading an aromatic compound and a chlorinated aliphatic hydrocarbon compound constitutively.

25. A method according to claim 24, wherein said aromatic compounds are at least one organic compound selected from phenol, toluene and cresol.

26. A method according to claim 24, wherein said chlorinated aliphatic hydrocarbon compounds are at least one organic compound selected from trichloroethylene and dichloroethylene.

27. A method for remedying an environment contaminated with a pollutant comprising: a step of decomposing the pollutant by contacting with a biologically pure culture of microorganism strain JM6U identified by Deposit No. (FERM BP-5962), wherein the strain JM6U is a mutant strain of strain J1 identified by Deposit No. (FERM BP-5102), and capable of degrading an aromatic compound and a chlorinated aliphatic hydrocarbon compound constitutively.

28. A method according to claim 27 wherein said environment is an aqueous medium.

29. A method according to claim 28 wherein said aqueous medium is made to contact with a carrier on which said microorganism is retained.

30. A method according to claim 29 wherein the carrier retaining said microorganism is placed in a container, said aqueous medium being introduced from one side and discharged from the other side of the container.

31. A method according to claim 27, wherein said environment is a soil.

32. A method according to claim 31, wherein said microorganism is contained in an aqueous medium, said aqueous medium being introduced into the soil.

33. A method according to claim 32, wherein said aqueous medium is introduced into the soil by applying a pressure through a injection well provided in the soil.

34. A method according to claim 31, wherein at least one of nutrients for said microorganism and oxygen is introduced into said soil.

35. A method according to claim 31, wherein said microorganism is made to incorporate into a liquid phase, followed by introducing said soil into said liquid phase.

36. A method according to claim 31, wherein said soil is made to contact with a carrier retaining said microorganism.

37. A method according to claim 27, wherein said environment is air.

38. A method according to claim 37, wherein said air is introduced into a liquid phase containing said microorganism.

39. A method according to claim 37, wherein said air is made to contact with a carrier retaining said microorganism.

40. A method according to claim 37, wherein said air is introduced from one side and discharged from the other side of a container that contains a carrier retaining the microorganism.

41. A method according to claim 27, wherein said pollutant is aromatic compounds.

42. A method according to claim 41, wherein said aromatic compound is at least one of phenol, toluene or cresol.

43. A method according to claim 27, wherein said pollutant is chlorinated aliphatic hydrocarbon compounds.

44. A method according to claim 43, wherein said chlorinated aliphatic hydrocarbon compound is at least one of trichloroethylene or dichloroethylene.

45. A biologically pure culture of microorganism strain JM7 identified by Deposit No. (FERM BP-5957), said strain JM7 being a mutant strain of strain J1 identified by Deposit No. (FERM BP-5102), and having an ability to degrade an aromatic compound and a chlorinated aliphatic hydrocarbon compound constitutively.

46. A method for biodegrading aromatic compounds or chlorinated aliphatic hydrocarbon compounds comprising: a step of bringing a biologically pure culture of a microorganism strain JM7 identified by Deposit No. (FERM BP-5957) into contact with the compounds to be degraded, wherein the strain JM7 is a mutant strain of strain J1 identified by Deposit No. (FERM BP-5102), and capable of degrading an aromatic compound and a chlorinated aliphatic hydrocarbon compound constitutively.

47. A method according to claim 46, wherein said aromatic compounds are at least one organic compound selected from phenol, toluene and cresol.

48. A method according to claim 46, wherein said chlorinated aliphatic hydrocarbon compounds are at least one organic compound selected from trichloroethylene and dichloroethylene.

49. A method for remedying an environment contaminated with a pollutant comprising: a step of decomposing the pollutant by contacting with a biologically pure culture of microorganism strain JM7 identified by Deposit No. (FERM BP-5957), wherein the strain JM7 is a mutant strain of strain J1 identified by Deposit No. (FERM BP-5102), and capable of degrading an aromatic compound and a chlorinated aliphatic hydrocarbon compound constitutively.

50. A method according to claim 49 wherein said environment is an aqueous medium.

51. A method according to claim 50, wherein said aqueous medium is made to contact with a carrier on which said microorganism is retained.

52. A method according to claim 51, wherein the carrier retaining said microorganism is placed in a container, said aqueous medium being introduced from one side and discharged from the other side of the container.

53. A method according to claim 49, wherein said environment is a soil.

54. A method according to claim 53, wherein said microorganism is contained in an aqueous medium, said aqueous medium being introduced into said soil.

55. A method according to claim 54, wherein said aqueous medium is introduced into soil by applying a pressure through a injection well provided in the soil.

56. A method according to claim 53, wherein at least one of nutrients for said microorganism and oxygen is introduced into said soil.

57. A method according to claim 53, wherein said microorganism is made to incorporate into a liquid phase, followed by introducing said soil into said liquid phase.

58. A method according to claim 53, wherein said soil is made to contact with a carrier retaining said microorganism.

59. A method according to claim 49, wherein said environment is air.

60. A method according to claim 59, wherein said air is introduced into a liquid phase containing said microorganism.

61. A method according to claim 59, wherein said air is made to contact with a carrier retaining said microorganism.

62. A method according to claim 59, wherein said air is introduced from one side and discharged from the other side of a container that contains a carrier retaining the microorganism.

63. A method according to claim 49, wherein said pollutant is aromatic compounds.

64. A method according to claim 63, wherein said aromatic compound is at least one of phenol, toluene or cresol.

65. A method according to claim 49, wherein said pollutant is a chlorinated aliphatic hydrocarbon compounds.

66. A method according to claim 65, wherein said chlorinated aliphatic hydrocarbon compound is at least one of trichloroethylene or dichloroethylene.

* * * * *

UNITED STATES PATENT AND TRADEMARK OFFICE
CERTIFICATE OF CORRECTION

PATENT NO. : 5,945,331
DATED : August 31, 1999
INVENTOR(S) : SHINYA KOZAKI ET AL.

It is certified that error appears in the above-identified patent and that said Letters Patent is hereby corrected as shown below:

ON THE TITLE PAGE

[56] References Cited, under OTHER PUBLICATIONS:

After "Tsien, et al.": "Trichloroethelene" should read --Trichloroethylene--;
      After "Shields, et al.,": "Trichloroethelene" should read --Trichloroethylene--; and
      After "Nakajima, et al.,": "(1992).Nakajima, et al.," should read --(1992). ¶Nakajima, et al.,--.

COLUMN 1

Line 19, "precession" should read --precision--.

COLUMN 2

Line 38, "view point" should read --viewpoint--; and
    Line 45, "an" should read --a--.

COLUMN 4

Line 34, "coexisting" should read --coexisting with--.

COLUMN 5

Line 16, "in" (second occurrence) should be deleted.
    Line 32, "in" should read --on--; and
    Line 34, "BP5957)" should read --BP-5957)--.

UNITED STATES PATENT AND TRADEMARK OFFICE
CERTIFICATE OF CORRECTION

PATENT NO. : 5,945,331

DATED : August 31, 1999

INVENTOR(S) : SHINYA KOZAKI ET AL.

It is certified that error appears in the above-identified patent and that said Letters Patent is hereby corrected as shown below:

COLUMN 6

Line 50, "strain JMN2," should read --strains JMN2,--.

COLUMN 12

Line 49, "(Tsukubashi," should read --(Tsukuba-shi,--.

COLUMN 16

Line 47, "JM2" should read --JM2N--.

COLUMN 17

Line 3, "a" should read --an--.

COLUMN 18

Line 7, "a" should read --an--.

COLUMN 19

Line 14, "soil" should read --the soil--; and
Line 15, "a" should read --an--.

UNITED STATES PATENT AND TRADEMARK OFFICE
CERTIFICATE OF CORRECTION

PATENT NO. : 5,945,331
DATED : August 31, 1999
INVENTOR(S) : SHINYA KOZAKI ET AL.

It is certified that error appears in the above-identified patent and that said Letters Patent is hereby corrected as shown below:

COLUMN 20

Line 17, "a" should be deleted.

Signed and Sealed this

Thirtieth Day of May, 2000

Attest:

Attesting Officer

Q. TODD DICKINSON
Director of Patents and Trademarks